United States Patent [19]

Langbein et al.

[11] 4,004,010
[45] Jan. 18, 1977

[54] PHARMACEUTICAL COMPOSITIONS CONTAINING AN N-(FURYL-METHYL)-7α-ACYL-6,14-(ENDOETHENO OR ENDOETHANO)-TETRAHYDRO-NORORIPAVINE OR -NORTHEBAINE AND METHOD OF USE

[75] Inventors: Adolf Langbein; Herbert Merz; Gerhard Walther; Klaus Stockhaus, all of Ingelheim am Rhein, Germany

[73] Assignee: Boehringer Ingelheim GmbH, Ingelheim am Rhein, Germany

[22] Filed: Oct. 30, 1975

[21] Appl. No.: 627,286

Related U.S. Application Data

[62] Division of Ser. No. 369,499, June 13, 1973, Pat. No. 3,931,187.

[30] Foreign Application Priority Data

June 19, 1972   Germany .......................... 2229770

[52] U.S. Cl. .................................................. 424/260
[51] Int. Cl.² ...................................... A61K 31/485
[58] Field of Search ......................... 424/285, 260

*Primary Examiner*—Stanley J. Friedman
*Attorney, Agent, or Firm*—Hammond & Littell

[57] ABSTRACT

Pharmaceutical compositions containing as an active ingredient a compound of the formula

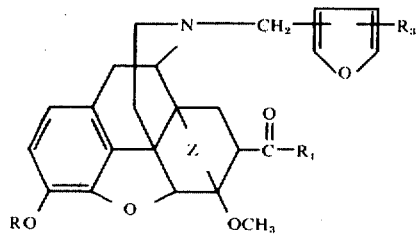

wherein
R is hydrogen, methyl or acetyl,
$R_1$ is methyl, phenyl or hydrogen,
Z is —CH=CH— or —CH$_2$—CH$_2$—, and
$R_3$ is hydrogen or methyl,
and non-toxic, pharmacologically acceptable acid addition salts thereof; and a method using the same as analgesics and antitussives.

10 Claims, No Drawings

PHARMACEUTICAL COMPOSITIONS CONTAINING AN N-(FURYL-METHYL)-7α-ACYL-6,14-(ENDOETHENO OR ENDOETHANO)-TETRAHYDRO-NORORIPAVINE OR -NORTHEBAINE AND METHOD OF USE

This is a division of copending application Ser. No. 369,499 filed June 13, 1973, now U.S. Pat. No. 3,931,187 granted Jan. 6, 1976.

This invention relates to novel pharmaceutical compositions containing an N-(furyl-methyl)-7α-acyl-6,14-(endoetheno or endoethano)-tetrahydro-nororipavine or -northebaine or a non-toxic acid addition salt thereof, as well as to a method of using the same as analgesics and antitussives.

THE PRIOR ART

In J.A.C.S. 89, 3267 (1967) it is disclosed that some Diels-Alder adducts of vinyl ketones and thebaine or oripavine, that is, adducts of the opium alkaloids of the formula

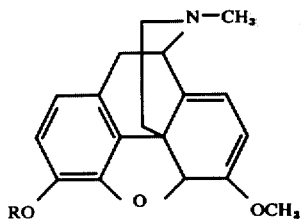

wherein R is hydrogen (oripavine) or methyl (thebaine), are strong central analgesics.

Furthermore, published Dutch application No. 6,805,648 and U.S. Pat. No. 3,562,279 disclose that certain N-(allyl or cyclopropylmethyl)-7-acyl-6,14-(endoethano or endoetheno)-derivatives of these opium alkaloids, that is, compounds of the formula

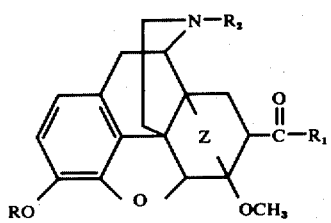

wherein
R is hydrogen or methyl,
$R_1$ is hydrogen, methyl, or phenyl,
$R_2$ is allyl or cyclopropylmethyl, and
Z is —CH=CH— or —CH$_2$—CH$_2$—,
exhibit analgesic and opiate-antagonistic properties in laboratory animals.

THE INVENTION

More particularly, the present invention relates to novel pharmaceutical compositions containing as an active ingredient an N- furylmethyl -7α-carboxylic acyl-6,14-(endoethano or endoetheno)-tetrahydro-nororipavine or -northebaine of the formula

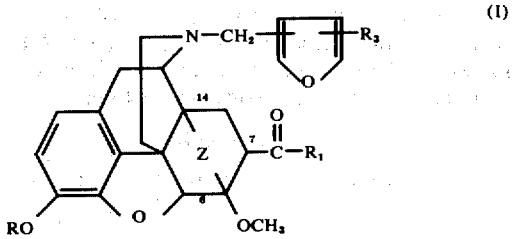

wherein
R is hydrogen, methyl, or acetyl,
$R_1$ is methyl, phenyl or hydrogen,
Z is —CH=CH— or —CH$_2$—CH$_2$—, and
$R_3$ is hydrogen or methyl,
or a non-toxic, pharmacologically acceptable acid addition salt thereof.

The compounds may form isomers in the 7-position; "7α" means that the carboxylic acyl substituent lies below the plane of the paper.

The compounds embraced by formula I may be prepared by the following methods.

Method A

By reacting an oripavine or thebaine derivative of the formula

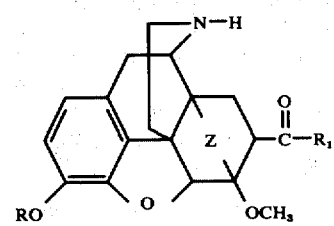

wherein R, $R_1$ and Z have the same meanings as in formula I, with a furylmethyl derivative of the formula

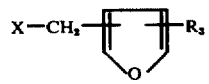

wherein
$R_3$ has the meanings previously defined, and
X is halogen, preferably chlorine, bromine or iodine, alkyl—SO$_2$—O—, aryl—SO$_2$—O— or trialkyl- ammonium, preferably (CH$_3$)$_3$—N—.

The reaction of the compound of the formula II is performed with the calculated amount, or a slight excess thereover, of the furylmethyl derivative of the formula III, optionally in the presence of an acid-binding agent. Examples of suitable acid-binding agents are tertiary amines, such as triethylamine or N,N.-dicyclohexyl-ethylamine; alkali metal carbonates, such as sodium carbonate or potassium carbonate; alkali metal bicarbonates, preferably sodium bicarbonate; or alkali metal hydroxides or oxides. The reaction is advantageously carried out in an inert organic solvent medium, such as tetrahydrofuran, dioxane, methylene chloride, dimethylformamide, dimethylsulfoxide or a mixture of two or more of these, preferably mixtures of tetrahydrofuran and dimethylformamide. The reaction temperature may vary within wide limits, but a temperature between 0° C and the boiling point of the particular solvent medium which is used is preferred. After completion of the reaction, the reaction product is isolated and crystallized by conventional methods.

Method B

By ketal cleavage of a compound of the formula

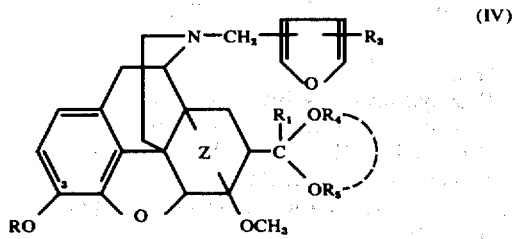

wherein R, $R_1$, $R_3$ and Z have the same meanings as in formula I, and $R_4$ and $R_5$, which may be identical to or different from each other, are each alkyl of 1 to 10 carbon atoms or aryl, particularly phenyl, or, together with each other, alkylene of 2 to 8 carbon atoms.

The ketal cleavage is effected with a dilute acid, preferably a dilute mineral acid, such as dilute hydrochloric or sulfuric acid, normally at room temperature or moderately elevated temperatures up to 100° C, for example. In those instances where the ketal cleavage reaction is applied to a compound of the formula IV wherein R is carboxylic acyl, the 3-substituent is simultaneously converted into phenolic hydroxyl, and the end product is a corresponding compound of the formula I wherein R is hydrogen.

Method C

By reacting a compound of the formula II with formaldehyde and a furan of the formula

wherein $R_3$ has the meanings defined above.

The reaction is carried out in weakly acid solution, especially in an acetic acid solution, and preferably in aqueous 50% acetic acid. Other suitable solvents are water, lower alkanols, tetrahydrofuran, dioxane or mixtures of any two or more of these. The furan of the formula V is provided in the stoichiometric amount or in slight excess thereover, either dissolved or suspended in the solvent medium. The formaldehyde may be provided in the form of paraformaldehyde or preferably in the form of an aqueous solution in the calculated amount or in excess thereover. The reaction temperature may vary between −10° C and the boiling point of the particular solvent medium which is employed, but the preferred temperature is 25° C. After completion of the reaction, the reaction product is isolated and crystallized by conventional methods.

Method D

By reacting a compound of the formula II with a furaldehyde of the formula

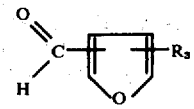

wherein $R_3$ has the meanings previously defined, in the presence of formic acid.

The reaction may be effected in aqueous solution, as well as in suitable organic solvents or mixtures of solvents, or also in 100% formic acid without the addition of a separate solvent. The aldehyde of the formula V is used in the calculated quantity or in excess thereover, preferably in an amount of up to 1.5 mols of aldehyde per mol of the compound of the formula II. The formic acid is advantageously provided in excess, preferably in an amount of 2 to 5 mols per mol of compound II. The reaction is carried out at temperatures between 50° and 200° C, preferably between 80° and 150° C. The reaction product is isolated by conventional methods.

Method E

For the preparation of a compound of the formula I wherein Z is —CH=CH—, by reacting an N (furylmethyl)-northebaine or -nororipavine of the formula

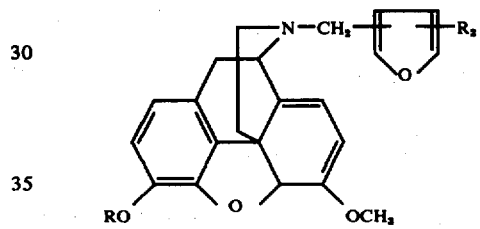

wherein R and $R_3$ have the same meanings as in formula I, with a vinyl ketone of the formula

wherein $R_1$ has the same meanings as in formula I.

This Diels-Alder addition is carried out by reacting a compound of the formula VII with a freshly distilled vinyl ketone of the formula VIII in a suitable inert solvent, preferably benzene, at a temperature between 0° C and the boiling point of the solvent, preferably at the reflux temperature of the reaction mixture. The reaction product is isolated and crystallized by conventional methods after completion of the reaction.

Method F

For the preparation of a compound of the formula I wherein R is methyl or acetyl, by methylating or acetylating, respectively, a compound of the formula I wherein R is hydrogen.

The methylation is effected in conventional manner, that is, by reacting the starting compound with a conventional methylating agent, such as diazomethane, a methyl ester of an inorganic acid, preferably dimethyl sulfate, or a phenyl trimethylammonium compound.

The acetylation is effected with conventional acetylating agents, such as an acetyl halide, preferably acetyl chloride or acetic acid anhydride.

The starting compounds required for methods A to D are, to a large extent, known compounds or may be prepared by known methods.

For instance, a compound of the formula II may be obtained by first converting a Diels-Alder adduct of thebaine and a vinyl ketone of the formula

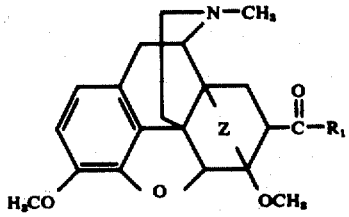

(IX)

wherein $R_1$ and Z have the same meanings as in formula I, into a ketal of the formula

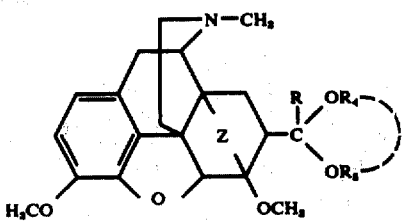

(X)

wherein $R_1$, $R_4$, $R_5$ and Z have the meanings previously defined, subjecting the latter to cyanogen bromide degradation to form the corresponding northebaine derivative of the formula

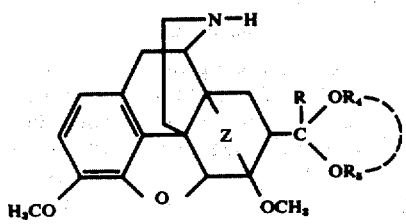

(XI)

wherein $R_1$, $R_4$, $R_5$ and Z have the meanings previously defined, and subjecting the northebaine derivative to alkaline ether cleavage to form the corresponding nororipavine derivative of the formula

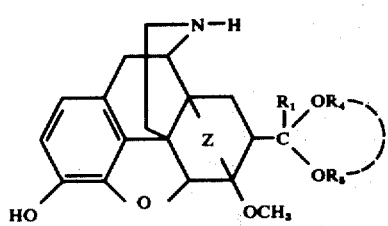

(XII)

wherein $R_1$, $R_4$, $R_5$ and Z have the meanings previously defined. Hydrolysis of the ketals of the formulas XI and XII yields the corresponding ketones of the formula II.

An O-acetyl derivative of the formula II is obtained, for example, by benzylating a ketal of the formula XII, subjecting the benzylation product to alkaline anisole cleavage to form the corresponding 3-hydroxy compound, followed by acetylation, de-benzylation and ketal cleavage.

A compound of the formula IV may be prepared by reacting a ketal of the formula XI or XII with a compound of the formula III, or by reacting a ketal of the formula XI or XII with an acyl halide of the formula

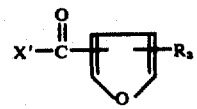

(XIII)

wherein $R_3$ has the meanings previously defined and X' is halogen, preferably chlorine, to form a ketal of the formula

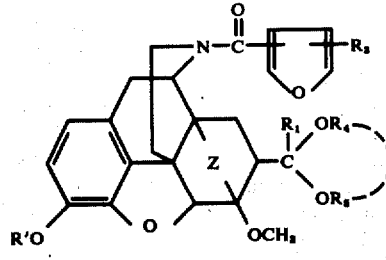

(XIV)

wherein $R_1$, $R_3$, $R_4$, $R_5$ and Z have the same meanings as in formula I and R' is hydrogen or methyl, followed by reduction of compound XIV with a complex metal hydride, such as lithium aluminum hydride.

By acetylation of a compound of the formula IV wherein R is hydrogen the corresponding O-acetyl derivative is obtained.

A compound of the formula VII is obtained by alkylating northebaine or nororipavine with a compound of the formula III; or also by acylating northebaine or nororipavine with an acyl halide of the formula XIII, followed by reduction with a complex metal hydride, preferably lithium aluminum hydride. The reduction with a complex metal hydride simultaneously splits off an O-acyl group, wherefor this process always yields a compound of the formula VII wherein R is hydrogen. This 3-hydroxy-substituted derivative may then be converted into the corresponding 3-acetoxy-substituted compound by acetylation in conventional manner.

The 6,14-endoetheno compounds of the formulas II, IV, IX, XI, XII and XIV, i.e., those wherein Z is —CH=CH—, may readily be converted into their saturated 6,14-endoethano analogs, i.e., wherein Z is —CH$_2$—CH$_2$—, by catalytic hydrogenation.

The compounds embraced by formulas III, V, VI and VIII are all known compounds, and many of them are readily available in commerce.

The compounds of the formula I are bases and therefore form acid addition salts with inorganic or organic acids. Examples of non-toxic, pharmacologically acceptable acid addition salts are those formed with hydrochloric acid, hydrobromic acid, hydriodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid, citric acid, malic acid, benzoic acid, phthalic acid, cinnamic acid, salicylic acid, ascorbic acid, 8-chlorotheophylline, methanesulfonic acid, ethanephosphonic acid or the like.

The following examples illustrate the preparation of various compounds of the formula I.

EXAMPLE 1

N-(2'-Methyl-3'-furylmethyl)-7α-acetyl-6,14-endoetheno-tetrahydro-northebaine and its hydrochloride by method A A mixture consisting of 4.04 gm (0.01 mol) of 6,14-endoetheno-7α-acetyl-tetrahydro-northebaine hydrochloride, 2.52 gm (0.03 mol) of sodium bicarbonate, 1.43 gm (0.011 mol) of 2-methyl-3-chloromethyl-furan and 50 ml of a 2:1 mixture of tetrahydrofuran and dimethylformamide was refluxed for four hours. Thereafter, the reaction mixture was evaporated in vacuo, the residue was taken up in methylene chloride, and the resulting solution was washed six times with water, dried with sodium sulfate and evaporated in vacuo, leaving as a residue 4.6 gm of the free base N-(2'-methyl-3'-furyl-methyl)-7α-acetyl-6,14-endoetheno-tetrahydro-northebaine.

The free base was dissolved in 10 ml of ethanol, the resulting solution was acidified with 2 ml of 5 N ethanolic hydrocloric acid, and then 10 ml of ether were added, whereby a crystalline substance separated out which was collected. 3 gm (60% of theory) of the hydrochloride of the formula

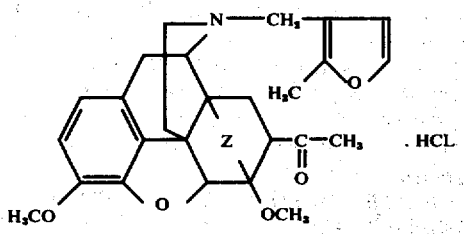

where Z is —CH=CH—, were obtained. The hydrochloride had a melting point of 172°–174° C (foaming).

EXAMPLE 2

Using a procedure analogous to that described in Example 1, N-furfuryl-6,14-endoetheno-7α-acetyl-tetrahydro-northebaine and 29% of theory of its hydrochloride, m.p. 187°–190° C, were obtained from 6,14-endoetheno-7α-acetyl-tetrahydro-northebaine hydrochloride and furfuryl chloride.

EXAMPLE 3

Using a procedure analogous to that described in Example 1, N-(3'-furylmethyl)-6,14-endoetheno-7α-acetyl-tetrahydro-northebaine and 86% of theory of its hydrochloride were obtained from 6,14-endoetheno-7α-acetyl-tetrahydro-northebaine hydrochloride and 3-chloromethyl-furan.

Since neither the free base nor the hydrochloride could be crystallized, the base was purified by chromatography on aluminum oxide (activity II, neutral) with chloroform, and the hydrochloride was dried as a foam. $R_f$-value: 0.7 (thin-layer chromatogram on silicagel; flow agent: Chloroform/methanol/ammonia = 90:9:1 ml).

EXAMPLE 4

Using a procedure analogous to that described in Example 1, N-furfuryl-6,14-endoetheno-7α-acetyl-tetrahydro-nororipavine and 55% of theory of its hydrochloride, m.p. 210°–215° C, were obtained from 6,14-endoetheno-7α-acetyl-tetrahydro-nororipavine and furfuryl chloride.

EXAMPLE 5

Using a procedure analogous to that described in Example 1, N-(3'-furylmethyl)-6,14-endoetheno-7α-acetyl-tetrahydro-nororipavine and 57% of theory of its hydrochloride, m.p. 228° C (decomp.), were obtained from 6,14-endoetheno-7α-acetyl-tetrahydro-nororipavine and 3-chloromethyl-furan.

EXAMPLE 6

Using a procedure analogous to that described in Example 1, N-(2'-methyl-3'-furylmethyl)-6,14-endoetheno-7α-acetyl-tetrahydro-nororipavine and 76% of theory of its hydrochloride, m.p. 185° C (decomp.), were obtained from 6,14-endoetheno-7α-acetyl-tetrahydro-nororipavine and 2-methyl-3-chloromethyl-furan.

EXAMPLE 7

Using a procedure analogous to that described in Example 1, 71% of theory of N-furfuryl-6,14-endoetheno-7α-benzoyl-tetrahydro-northebaine, m.p. 164°–166° C, was obtained from 6,14-endoetheno-7α-benzoyl-tetrahydro-northebaine and furfuryl chloride.

EXAMPLE 8

Using a procedure analogous to that described in Example 1, 73% of theory of N-(3'-furylmethyl)-6,14-endoetheno-7α-benzoyl-tetrahydro-northebaine, m.p. 148°–150° C, was obtained from 6,14-endoetheno-7α-benzoyl-tetrahydro-northebaine and 3-chloromethyl-furan.

EXAMPLE 9

Using a procedure analogous to that described in Example 1, N-(2'-methyl-3'-furylmethyl)-6,14-endoetheno-7α-benzoyl-tetrahydro-northebaine and 68% of theory of its hydrochloride, m.p. 180°–184° C, were obtained from 6,14-endoetheno-7α-benzoyl-tetrahydro-northebaine and 2-methyl-3-chloromethyl-furan.

EXAMPLE 10

Using a procedure analogous to that described in Example 1, 67% of theory of N-furfuryl-6,14-endoethano-7α-acetyl-tetrahydro-northebaine, m.p. 111°–112° C, was obtained from 6,14-endoethano-7α-acetyl-tetrahydro-northebaine and furfuryl chloride.

EXAMPLE 11

Using a procedure analogous to that described in Example 1, 59.4% of theory of N-(3'-furylmethy)-6,14-endoethano-7α-acetyl-tetrahydro-northebaine, m.p. 104°–106° C, was obtained from 6,14-endoethano-7α-acetyl-tetrahydro-northebaine and 3-chloromethyl-furan.

EXAMPLE 12

Using a procedure analogous to that described in Example 1, N-(2'-methyl-3'-furylmethyl)-6,14-endoethano-7α-acetyl-tetrahydro-northebaine and 67% of theory of its hydrochloride, m.p. 175°–178° C, were obtained from 6,14-endoethano-7α-acetyl-tetrahydro-northebaine and 2-methyl-3-chloromethyl-furan.

EXAMPLE 13

N-(3'-Methyl-furfuryl)-6,14-endoetheno-7α-acetyl-tetrahydro-nororipavine by method B 1.7 gm (4.26 millimols) of 6,14-endoetheno-7α-(1',1'-dimethoxy-ethyl)-tetrahydro-nororipavine were suspended in 25 ml of methanol, the suspension was admixed with a solution of 1.06 gm (7.67 millimols) of potassium carbonate in 4 ml of water, and, while cooling the resulting mixture, 0.676 gm (4.7 millimols) of 3-methyl-furan-2-carboxylic acid chloride was added dropwise thereto over a period of 20 minutes. The resulting mixture was stirred for 1 hour and was thereafter evaporated in vacuo. The residue was dissolved in methylene chloride, the resulting solution was washed several times with water, then with dilute hydrochloric acid, subsequently with dilute sodium bicarbonate solution and finally again with water, and the organic phase was dried over sodium sulfate and evaporated in vacuo. The residue was dissolved in 18 ml of absolute tetrahydrofuran, the resulting solution was added dropwise to a suspension of 0.323 gm (8.52 millimols) of lithium aluminum hydride in 18 ml of absolute tetrahydrofuran, and the mixture was stirred for 1 hour. Thereafter, 50 ml of a saturated aqueous diammonium tartrate solution were added, and the aqueous phase was separated and washed twice with methylene chloride. The tetrahydrofuran phase was evaporated, the residue was dissolved in the combined methylene chloride wash solutions, and the resulting solution was washed several times with water, dried over sodium sulfate and evaporated.

For the purpose of effecting the ketal cleavage, the residue was dissolved in dilute sulfuric acid, the resulting solution was stirred for half an hour, made alkaline with ammonia and extracted with methylene chloride, and the organic extract solution was dried over sodium sulfate and again evaporated in vacuo. The residue was recrystallized from a little methanol, yielding 0.3 gm (16% of theory) of N-(3'-methyl-furfuryl)-6,14-endoetheno-7α-acetyl-tetrahydro-nororipavine with a melting point of 198°-200° C.

EXAMPLE 14

N-(3'-Furylmethyl)-6,14-endoetheno-7α-formyl-tetrahydro-northebaine and its hydrochloride by method E A solution of 2.97 gm (0.01 mol) of northebaine, 1.26 gm of sodium bicarbonate and 1.2 gm (0.011 mol) of 3-chloromethyl-furan in 25 ml of tetrahydrofuran/dimethylformamide (2:1) was refluxed for 3 hours. Thereafter, the reaction mixture was evaporated in vacuo, the residue was dissolved in methylene chloride, the resulting solution was washed several times with water, and the organic phase was dried over sodium sulfate and evaporated. The residue was chromatographed with chloroform on basic aluminum oxide (activity III), yielding 1.8 gm of N-(3-furylmethyl)-northebaine.

The product thus obtained was dissolved in 50 ml of benzene, the resulting solution was admixed with 2 ml of acrolein, and the mixture was refluxed for 40 hours. Thereafter, the reaction solution was evaporated in vacuo, the residue was dissolved in dilute hydrochloric acid, and the solution was extracted twice with benzene. The aqueous phase was made alkaline with ammonia and was then extracted with methylene chloride, and the organic extract solution was dried over sodium sulfate and evaporated in vacuo, leaving 1.3 gm of an oil which was identified to be the free base N-(3'-furylmethyl)-6,14-endoetheno-7α-formyl-tetrahydro-northebaine.

The free base was admixed with ethanolic hydrochloric acid, and the solid substance formed thereby was collected and recrystallized from ethanol/ether, yielding 1.3 gm (about 28% of theory) of the hydrochloride which had a melting point of 190°-193° C.

EXAMPLE 15

Using a procedure analogous to that described in Example 14, N-furfuryl-6,14-endoethano-7α-formyl-tetrahydro-northebaine and 18% of theory of its chromatographically pure hydrochloride of the formula

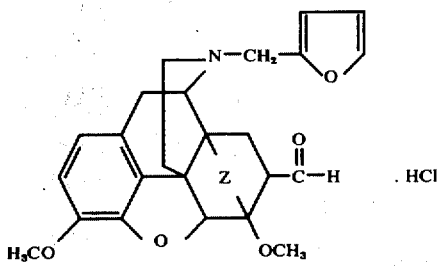

wherein Z is —CH₂—CH₂—, were obtained. The hydrochloride could not be crystallized and was dried as a foam.

EXAMPLE 16

Using a procedure analogous to that described in Example 14, 37% of theory of N-(2'-methyl-3'-furylmethyl)-6,14-endoetheno-7α-formyl-tetrahydro-northebaine, m.p. 117°-120° C, was obtained from northebaine, 2-methyl-3-chloromethyl-furan and acrolein.

EXAMPLE 17

N-(3'-Methyl-furfuryl)-6,14-endoetheno-7α-formyl-tetrahydro-northebaine by method E A suspension of 2.97 gm (0.01 mol) of northebaine in 50 ml of methanol was admixed with a solution of 2.5 gm of potassium carbonate in 4 ml of water, the mixture was cooled to 10° C, 174 gm (0.011 mol) of 3-methyl-furan-2-carboxylic acid chloride were added over a period of 10 minutes and the resulting mixture was vigorously stirred for 5 hours. Thereafter, the methanol was removed from the reaction mixture by evaporation, and the residue was shaken with a mixture of methylene chloride and water. The organic phase was separated, washed twice with 2 N hydrochloric acid and twice with water, dried with sodium sulfate and evaporated in vacuo, leaving a light oil which was immediately dissolved in 50 ml of absolute tetrahydrofuran. The resulting solution was added dropwise at 5° to 10° C to a suspension of 0.76 gm (0.02 mol) of lithium aluminum hydride in 25 ml of tetrahydrofuran, while stirring, and the resulting mixture was stirred overnight at room temperature. Thereafter, the reaction mixture was placed on an ice bath and, while vigorously stirring, 1.5 ml of water were added dropwise, the mixture was then admixed with 75 ml of a saturated aqueous diammonium tartrate solution, stirred for 1 hour and allowed to separate in a separator funnel. The tetrahydrofuran (upper) phase was isolated and evaporated; the aqueous phase was extracted three times with methylene chloride. The evaporation residue of the tetrahydrofuran phase was dissolved in the combined methylene chloride phases, and the resulting solution was washed several times with water, dried over sodium sulfate and evaporated. The residual oil was recrystallized from methanol, yielding 2 gm of N-(3-methyl-furfuryl)-northebaine with a melting point of 151°–154 ° C.

All of the product thus obtained was dissolved in 150 ml of benzene, the solution was admixed with 3 ml of acrolein, and the mixture was refluxed for 40 hours. Thereafter, the reaction mixture was worked up as described in Example 20, yielding 1.3 gm (38% of theory) of N-(3'-methyl-furfuryl)-6,14-endoetheno-7α-formyl-tetrahydro-northebaine with a melting point of 112°–115° C.

EXAMPLE 18

N-Furfuryl-3-(0-acetyl)-6,14-endoetheno-7α-acetyl-tetrahydro-nororipavine by method F A mixture consisting of 4.33 gm (0.01 mol) of N-furfuryl-6,14-endoetheno-7α-acetyl-tetrahydro-nororipavine, 10 ml of acetic acid anhydride and 0.82 gm (0.01 mol) of sodium acetate was heated for 1 hour at 100° C. Thereafter, the reaction mixture was allowed to cool, was then poured over 100 gm of ice, and after an interval of 5 minutes the solution was made alkaline with aqueous 30% sodium hydroxide. The resulting suspension was extracted with methylene chloride, and the organic phase was washed several times with water and aqueous sodium bicarbonate, dried over sodium sulfate and evaporated in vacuo, yielding 2.6 gm (50% of theory) of the compound of the formula

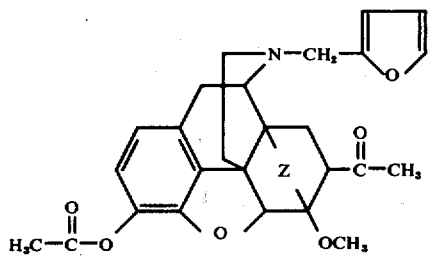

wherein Z is —CH=CH—, which had a melting point of 70°–71° C.

EXAMPLE 19

N-(5'-Methyl-furfuryl)-7α-acetyl-6,14-endoetheno-tetrahydro-northebaine and its hydrochloride by method C 4.04 gm (0.01 mol) of 6,14-endoetheno-7α-acetyl-tetrahydro-northebaine hydrochloride were converted into the free base with dilute aqueous ammonia in methylene chloride, the free base was dissolved in 10 ml of aqueous 50% acetic acid, and, while stirring the solution, 1.0 gm of aqueous 30% formaldehyde (0.01 mol formaldehyde) were added thereto. Subsequently, 0.82 gm (0.01 mol) of 2-methyl-furan was slowly added dropwise while stirring, and the resulting mixture was stirred at room temperature for 15 hours. Thereafter, the reaction mixture was admixed with ice and was then made alkaline with concentrated ammonia. The resulting aqueous mixture was now extracted with methylene chloride, and the organic extract solution was washed several times with water, dried over sodium sulfate and evaporated. The residue, the free base N-(5'-methyl-furfuryl)6,14-endoetheno-7α-acetyl-tetrahydro-northebaine, was treated with ethanolic hydrochloric acid, yielding 1.8 gm (39% of theory) of the hydrochloride which had a melting point of 180°–185° C.

The compounds embraced by formula I and their non-toxic, pharmacologically acceptable acid addition salts, have useful pharmacodynamic properties. More particularly, they exhibit non-narcotic analgesic and antitussive activities in warm-blooded animals, such as mice and rats.

All of the compounds of the present invention proved to be ineffective as analgesics in the Haffner test for analgesia [Deutsche Medizinische Wochenscrift 55, 731 (1929)]on mice and rats.

On the other hand, the compounds of this invention exhibit a distinct, dose-dependent analgesic activity in more sensitive pharmacological tests for analgesia, such as the hot-plate test [J. Pharmacol. Exp. Therap. 80, 300 (1944)]or the writhing test [J. Pharmacol. Exp. Therap. 154, 319 (1966)].

In accordance with presently prevailing teachings [Adv. Chem. Soc. 49, 162–169 (1964)], inactivity in the Haffner test is indicative of non-narcotic properties, while activity in the hot-plate test and/or writhing test proves analgesic properties.

For pharmaceutical purposes the compounds of the formula I or their non-toxic acid addition salts are administered to warm-blooded animals perorally, enterally or parenterally as active ingredients in customary dosages unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral analgesic and antitussive dosage unit of the compounds of the formula I or their non-toxic acid addition salts is from 0.016 to 6.7 mgm/kg body weight, preferably 0.41 to 3.4 mgm/kg body weight.

The following examples illustrate a few pharmaceutical dosage unit compositions comprising a compound of the formula I or a non-toxic acid addition salt thereof as an active ingredient and represent the best modes contemplated of putting the invention into practical use. The parts are parts by weight unless otherwise specified.

EXAMPLE 20

Tablets

The tablet composition is compounded from the following ingredients

| | |
|---|---|
| N-Furfuryl-7α-acetyl-6,14-endoetheno-tetrahydro-northebaine hydrochloride | 50.0 parts |
| Lactose | 95.0 parts |
| Corn starch | 45.0 parts |
| Colloidal silicic acid | 2.0 parts |
| Soluble starch | 5.0 parts |

-continued

| | | |
|---|---|---|
| Magnesium stearate | | 3.0 parts |
| | Total | 200.0 parts |

Preparation

The northebaine compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 50 mgm of the northebaine compound and is an oral dosage unit composition with effective analgesic and antitussive actions.

EXAMPLE 21

Coated Pills

The pill core composition is compounded from the following ingredients:

| | | |
|---|---|---|
| N-Furfuryl-6,14-endoetheno-7α-acetyl-tetrahydro-northebaine hydrochloride | | 75.0 parts |
| Lactose | | 100.0 parts |
| Corn starch | | 65.0 parts |
| Colloidal silicic acid | | 2.0 parts |
| Soluble starch | | 5.0 parts |
| Magnesium stearate | | 3.0 parts |
| | Total | 250.0 parts |

Preparation

The ingredients are compounded in the same manner as in Example 20, and the composition is compressed into 250 mgm-pill cores which are subsequently coated with a thin shell consisting essentially of a mixture of sugar, talcum and gum arabic and finally polished with beeswax. Each coated pill contains 75 mgm of the northebaine compound and is an oral dosage unit composition with effective analgesic and antitussive activities.

EXAMPLE 22

Suppositories

The suppository composition is compounded from the following ingredients:

| | | |
|---|---|---|
| N-(3''-Furylmethyl)-6,14-endoetheno-7α-acetyl-tetrahydro-northebaine hydrochloride | | 50.0 parts |
| Lactose | | 250.0 parts |
| Suppository base (e.g. cocoa butter) | | 1400.0 parts |
| | Total | 1700.0 parts |

Preparation

The northebaine compound is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 50 mgm of the northebaine compound and is a rectal dosage unit composition with effective analgesic and antitussive actions.

EXAMPLE 23

Hypodermic Solution

The solution is compounded from the following ingredients:

| | | |
|---|---|---|
| N-(2'-Methyl-3'-furylmethyl)-6,14-endoetheno-7α-acetyl-tetrahydro-northebaine hydrochloride | | 75.0 parts |
| Sodium chloride | | 5.0 parts |
| Double-distilled water | q.s.ad | 2000.0 parts by vol. |

Preparation

The northebaine compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 75 mgm of the northebaine compound, and its contents are an injectable dosage unit composition with effective analgesic and antitussive actions.

EXAMPLE 24

Drop Solution

The solution is compounded from the following ingredients:

| | | |
|---|---|---|
| N-Furfuryl-6,14-endoetheno-7α-acetyl-tetrahydro-northebaine hydrochloride | | 0.70 parts |
| Methyl p-hydroxy-benzoate | | 0.07 parts |
| Propyl p-hydroxy-benzoate | | 0.03 parts |
| Demineralized water | q.s.ad | 100.0 parts by vol. |

Preparation

The northebaine compound and the p-hydroxy-benzoates are dissolved in the demineralized water, the solution is filtered, and the filtrate is filled into 100 ml-bottles. 10 ml of the solution contain 70 mgm of the northebaine compound and are an oral dosage unit composition with effective analgesic and antitussive actions.

Analogous results are obtained when any one of the other compounds embraced by formula I or a non-toxic acid addition salt thereof is substituted for the particular northebaine compound in Examples 20 through 24. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An analgesic or antitussive pharmaceutical dosage unit composition consisting essentially of an inert pharmaceutical carrier and an effective analgesic or antitussive amount of a compound of the formula

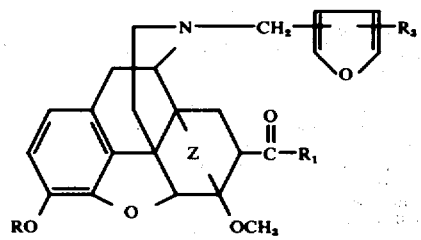

wherein
R is hydrogen, methyl or acetyl,
$R_1$ is methyl, phenyl or hydrogen,
Z is —CH=CH— or —$CH_2$—$CH_2$—, and
$R_3$ is hydrogen or methyl,
or a non-toxic, pharmacologically acceptable acid addition salt thereof.

2. A composition of claim 1, where
R is hydrogen,
$R_1$ is methyl or phenyl,
Z is —CH=CH— or —$CH_2$—$CH_2$—, and
$R_3$ is hydrogen, 3. A composition of claim 1 where said compound is N-furfuryl-6,14-endoetheno-7α-acetyl-tetrahydro-northebaine or a non-toxic, pharmacologically acceptable acid addition salt thereof.

4. A composition of claim 1, where said compound is N-(3'-furylmethyl)-6,14-endoetheno-7α-acetyl-tetrahydro-northebaine or a non-toxic, pharmacologically acceptable acid addition salt thereof.

5. A composition of claim 1, where said compound is N-(2'-methyl-3'-furylmethy)-6,14-endoetheno-7α-acetyl-tetrahydro-northebaine or a non-toxic, pharmacologically acceptable acid addition salt thereof.

6. The method of raising the pain threshold or suppressing the cough reflex in a warm-blooded animal, which comprises administering to said animal an effective analgesic or antitussive amount of a compound of the formula

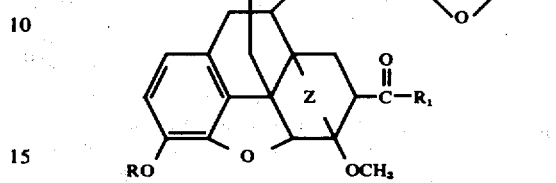

wherein
R is hydrogen, methyl or acetyl,
$R_1$ is methyl, phenyl or hydrogen,
Z is —CH=CH— or —$CH_2$—$CH_2$—, and
$R_3$ is hydrogen or methyl,
or a non-toxic, pharmacologically acceptable acid addition salt thereof.

7. The method of claim 6, where
R is hydrogen,
$R_1$ is methyl or phenyl,
Z is —CH=CH— or —$CH_2$—$CH_2$—, and
$R_3$ is hydrogen, 8. The method of claim 6, where said compound is N-furfuryl-6,14-endoetheno-7α-acetyl-tetrahydro-northebaine or a non-toxic, pharmacologically acceptable acid addition salt thereof.

9. The method of claim 6, where said compound is N-(3'-furyl-methyl)-6,14-endoetheno-7α-acetyl-tetrahydro-northebaine or a non-toxic, pharmacologically acceptable acid addition salt thereof.

10. The method of claim 6, where said compound is N-(2'-methyl-3'-furylmethyl)-6,14-endoetheno-7α-acetyl-tetrahydro-northebaine or a non-toxic, pharmacologically acceptable acid addition salt thereof.

* * * * *